(12) United States Patent
Overaker

(10) Patent No.: US 6,575,986 B2
(45) Date of Patent: Jun. 10, 2003

(54) SCAFFOLD FIXATION DEVICE FOR USE IN ARTICULAR CARTILAGE REPAIR

(75) Inventor: David W. Overaker, Annandale, NJ (US)

(73) Assignee: Ethicon, Inc., Somerville, NJ (US)

( * ) Notice: Subject to any disclaimer, the term of this patent is extended or adjusted under 35 U.S.C. 154(b) by 6 days.

(21) Appl. No.: 09/793,029

(22) Filed: Feb. 26, 2001

(65) Prior Publication Data

US 2002/0120281 A1 Aug. 29, 2002

(51) Int. Cl.$^7$ ................................................ A61B 17/56
(52) U.S. Cl. .................. 606/151; 606/72; 606/213; 411/508
(58) Field of Search ............................ 606/72, 73, 104, 606/151, 213; 411/392, 395, 486, 487, 508, 439, 500

(56) References Cited

U.S. PATENT DOCUMENTS

| | | |
|---|---|---|
| 3,929,971 A | 12/1975 | Roy |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,448 A | 2/1980 | Brekke |
| 4,205,399 A | 6/1980 | Shalaby et al. |
| 4,208,511 A | 6/1980 | Shalaby et al. |
| 4,861,733 A | 8/1989 | White |
| 5,067,964 A | 11/1991 | Richmond et al. |
| 5,084,051 A | 1/1992 | Tormala et al. |
| 5,133,755 A | 7/1992 | Brekke |
| 5,306,311 A | 4/1994 | Stone et al. |
| 5,314,478 A | 5/1994 | Oka et al. |
| 5,314,989 A | 5/1994 | Kennedy et al. |
| 5,403,347 A | 4/1995 | Roby et al. |
| 5,431,679 A | 7/1995 | Bennett et al. |
| 5,458,643 A | 10/1995 | Oka et al. |
| 5,464,929 A | 11/1995 | Bezwada et al. |
| 5,468,253 A | 11/1995 | Bezwada et al. |
| 5,486,359 A | 1/1996 | Caplan et al. |
| 5,502,159 A | 3/1996 | Liu et al. |
| 5,514,378 A | 5/1996 | Mikos et al. |

(List continued on next page.)

FOREIGN PATENT DOCUMENTS

| | | |
|---|---|---|
| EP | 0274898 | 7/1988 |
| EP | 0278583 | 8/1988 |
| EP | 0464163 | 1/1992 |
| EP | 1027897 | 8/2000 |
| EP | 1129675 | 9/2001 |
| WO | 9916478 | 4/1999 |
| WO | 0020354 | 4/2000 |

OTHER PUBLICATIONS

A.F. Tencer, et al., "Compressive Properties Of Polymer Coated Synthetic Hydroxapatite For Bone Grafting", Journal of Biomedical Materials Research, vol. 19, John Wiley & Sons, Inc., (1985), pp. 957–969.

Ainslie T. Young, "Microcellular Foams via Phase Separation" J. Vac. Sci. Technol. A 4 (3), American Vacuum Society, May/Jun. (1986), pp. 1128–1133.

(List continued on next page.)

Primary Examiner—Kevin Shaver
Assistant Examiner—Michael B. Priddy

(57) ABSTRACT

A device for attaching a tissue replacement scaffold to a bone has a platform positionable in substantially parallel relationship to the bone for retaining the tissue scaffold proximate to the bone. A post extends from the platform and is insertable into a hole formed in the bone. One or more ribs extend from a side surface of the post along a portion of its length. The ribs are mounted on opposing flexible members and establish an interference fit relative to the hole in the bone tissue. The ribs are urged radially outwardly by the flexible members and have a sharp edge that grips the sides of the hole in the bone such that the ribs restrict withdrawal of the device. Vertical ribs may also be included to prevent rotation of the device within the hole in the bone.

13 Claims, 3 Drawing Sheets

U.S. PATENT DOCUMENTS

| | | | |
|---|---|---|---|
| 5,522,895 | A | 6/1996 | Mikos |
| 5,595,751 | A | 1/1997 | Bezwada et al. |
| 5,597,579 | A | 1/1997 | Bezwada et al. |
| 5,607,474 | A | 3/1997 | Athanasiou et al. |
| 5,607,687 | A | 3/1997 | Bezwada et al. |
| 5,618,552 | A | 4/1997 | Bezwada et al. |
| 5,620,698 | A | 4/1997 | Bezwada et al. |
| 5,624,463 | A | 4/1997 | Stone et al. |
| 5,632,745 | A | 5/1997 | Schwartz |
| 5,645,850 | A | 7/1997 | Bezwada et al. |
| 5,648,088 | A | 7/1997 | Bezwada et al. |
| 5,677,355 | A | 10/1997 | Shalaby et al. |
| 5,686,091 | A | 11/1997 | Leong et al. |
| 5,698,213 | A | 12/1997 | Jamiolkowski et al. |
| 5,700,583 | A | 12/1997 | Jamiolkowski et al. |
| 5,711,960 | A | 1/1998 | Shikinami |
| 5,713,374 | A | 2/1998 | Pachence et al. |
| 5,716,413 | A | 2/1998 | Walter et al. |
| 5,749,874 | A | 5/1998 | Schwartz |
| 5,755,792 | A | 5/1998 | Brekke |
| 5,769,899 | A | 6/1998 | Schwartz et al. |
| 5,770,193 | A | 6/1998 | Vacanti et al. |
| 5,770,417 | A | 6/1998 | Vacanti et al. |
| 5,859,150 | A | 1/1999 | Jamiolkowski et al. |
| 5,984,927 | A * | 11/1999 | Wenstrom, Jr. et al ....... 606/72 |
| 6,103,255 | A | 8/2000 | Levene et al. |
| 6,209,178 | B1 * | 4/2001 | Wiese et al. ................... 24/458 |
| 6,251,143 | B1 * | 6/2001 | Schwartz et al. ......... 623/23.72 |
| 6,355,066 | B1 * | 3/2002 | Kim ......................... 623/13.14 |
| 6,371,958 | B1 | 4/2002 | Overaker |

OTHER PUBLICATIONS

Daniel Cohn, et al., "Biodegradable PEO/PLA Block Copolymers" Journal of Biomedical Materials Research, vol. 22, John Wiley & Sons, Inc., (1988), pp. 993–1009.

Allcock, "Polyphosphazenes", Encyclopedia of Polymer Science and Engineering, vol. 13, John Wiley & Sons, Inc., New York (1988), pp. 31–41.

D. Cohn, "New Tailor–Made Biodegradable Polymeric Biomaterials" Polymer Preprints, vol. 30, No. 1, Division of Polymer Chemistry, Inc., Dallas, Texas, (Apr. 1989), p. 498.

Shigenobu Matsuda, "Thermodynamics of Formations of Porous Polymeric Membrane from Solutions", Polymer Journal, vol. 23, No. 5, (1991), pp. 435–444.

Jorge Heller, "Poly(ortho esters)", Handbook Of Biodegradable Polymers, Harwood Academic Publishers, Netherlands, (1997), pp. 99–118.

J. Vandorpe, et al., "Biodegradable Polyphosphazenes For Biomedical Applications", Handbook Of Biodegradable Polymers, Harwood Academic Publishers, Netherlands, (1997), pp. 161–182.

John Kemnitzer, et al., "Degradable Polymers Derived From the Amino Acid L–Tyrosine", Handbook Of Biodegradable Polymers, Harwood Academic Publishers, Netherlands, (1997), pp. 251–272.

B. Kreklau, et al., "Tissue Engineering of Biphasic Joint Cartilage Transplants", Biomaterials 20, Elsevier Science Ltd., (1999), pp. 1743–1749.

Gabriele G. Niederauer, et al., "Evaluation of Multiphase Implants for Repair of Focal Osteochondral Defects in Goats", Biomaterials 21, Elsevier Science Ltd., (2000), pp. 2561–2574.

D. Schaefer, et al., "In Vitro Generation of Osteochondral Composites", Biomaterials 20, Elsevier Science Ltd., (2000), pp. 2599–2606.

Vicki Rosen, Ph.D, et al., "Chapter 1—Introduction and Goal", The Cellular and Molecular Basis of Bone Formation and Repair, R.G. Landes Company, Austin, Texas, (1995), pp. 1–41.

* cited by examiner

SCAFFOLD FIXATION DEVICE FOR USE IN ARTICULAR CARTILAGE REPAIR

FIELD OF THE INVENTION

The present invention relates to scaffold fixation devices useful in articular cartilage repair and more specifically to a device for fastening an articular cartilage scaffold to underlying bone.

BACKGROUND OF THE INVENTION

Articular cartilage is a tissue that covers the articulating surfaces between bones in joints, such as the knee or elbow, which is subject to catastrophic or repetitive stress injury. Various means have been proposed to address such injuries including repair via tissue engineering. Tissue engineering is defined as the application of engineering disciplines to either maintain existing tissue structures or to enable new tissue growth. This engineering approach generally includes the delivery of a tissue scaffold that serves as an architectural support onto which cells may attach, proliferate, and synthesize new tissue to repair a wound or defect. Surgical use of a tissue scaffold requires a fixation means to secure the scaffold to the bone beneath the wounded cartilage site. Secure fixation of the scaffold within the wound site is necessary for proper healing.

Frequently, scaffolds, prostheses and fasteners used in orthopedic applications are made from synthetic absorbable biocompatible polymers which are well known in the art. Such polymers typically are used to manufacture medical devices which are implanted in body tissue and absorb over time. Synthetic, absorbable, biocompatible aliphatic polyesters include homopolymers, copolymers (random, block, segmented and graft) of monomers such as glycolic acid, glycolide, lactic acid, lactide(d, l, meso and mixtures thereof), ε-caprolactone, trimethylene carbonate and p-dioxanone. Numerous U.S. Patents describe these polymers, including U.S. Pat. Nos. 5,431,679; 5,403,347; 5,314,989 and 5,502,159. Devices made of an absorbable material have the advantage that they are absorbed by the body after healing has occurred.

U.S. Pat. No. 5,067,964 describes an articular cartilage repair piece which includes a backing layer of non-woven, felted fibrous material which is either uncoated or covered by a coating of tough, pliable material. A number of means are disclosed for fastening the repair piece to the underlying bone. U.S. Pat. Nos. 5,306,311 and 5,624,463 describe a prosthetic, resorbable articular cartilage and methods of its fabrication and insertion. U.S. Pat. No. 5,713,374 describes an attachment method to hold a biomaterial in place until healing occurs. U.S. Pat. Nos. 5,632,745 and 5,749,874 and 5,769,899 describe a bioabsorbable cartilage repair system.

It is well know that there is wide variability in stiffness, strength, and other physical properties of human bone, and that the properties vary from site to site among humans. It is therefore challenging to design mechanical fasteners for fixing a prosthetic scaffold to bone because the mechanical function of the device must be able to accommodate a range of bone physical properties.

Accordingly, it would be advantageous to provide a scaffold fixation device which has a fixation means that can perform in a variety of human bone.

SUMMARY OF THE INVENTION

The limitations of prior art devices for attaching a tissue scaffold to bone tissue, are overcome by the present invention which includes an attachment device having a platform positionable in substantially parallel relationship to the bone tissue for retaining the tissue scaffold proximate to the bone tissue. A post extends from the platform and is insertable into a hole formed in the bone tissue. At least one rib extends from a surface of the post generally perpendicular to the axis of the post, the rib positioned intermediate the platform and a distal end of the post and establishing an interference fit relative to the hole in the bone tissue to prevent withdrawal of the device from a hole in the bone tissue into which it has been inserted.

DETAILED DESCRIPTION OF THE INVENTION

Figure 2:
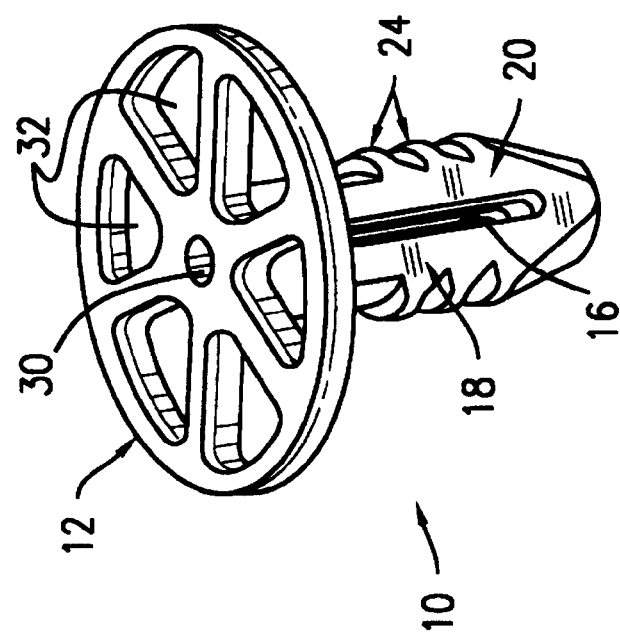
FIG. 2 is a perspective view of the device of FIG. 1.
Figure 1:
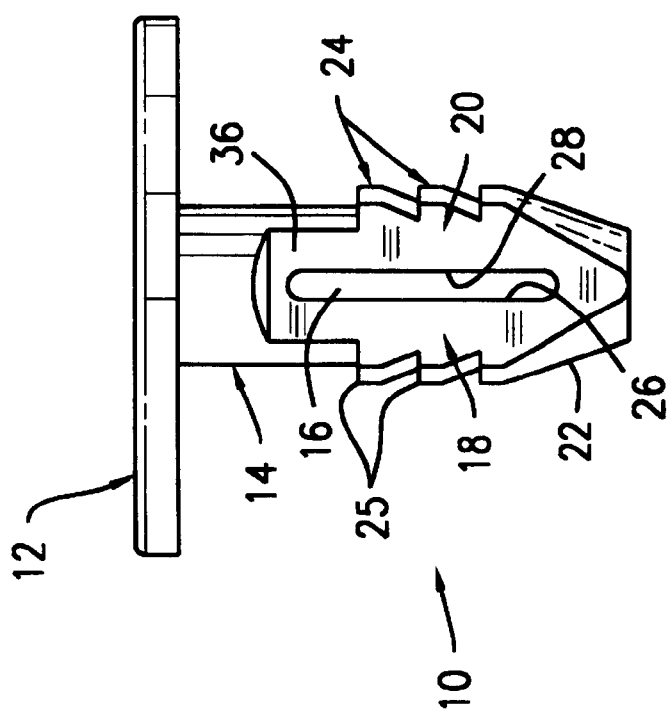
FIG. 1 is a side elevation view of a scaffold fixation device in accordance with an exemplary embodiment of the present invention.
Figure 3:
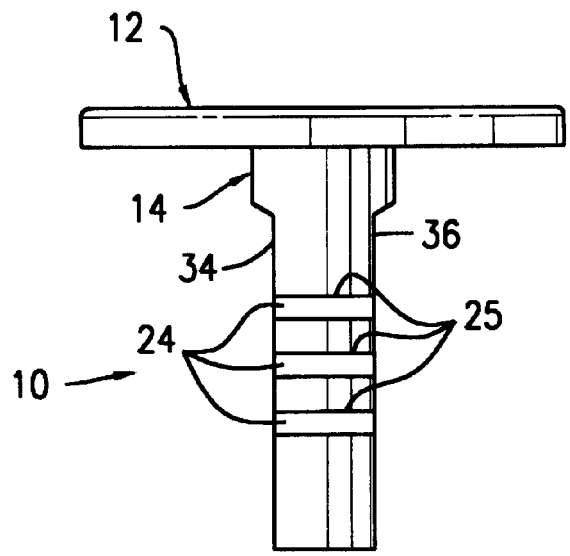
FIG. 3 is a front elevation view of the device of FIG. 1.

FIGS. 1, 2 and 3 show a scaffold fixation device 10 for fastening an articular cartilage scaffold to underlying bone. The device 10 has a scaffold attachment platform 12 with a post 14 extending therefrom. The post 14 has a central slot 16 defining a pair of flexible members, 18, 20 which are conjoined at one end proximate the platform 12 and at the other end proximate a tapered tip 22. One or more ribs 24 extend radially from the peripheral surface of the flexible members 18, 20. Each rib 24 terminates in a sharp ledge or tip 25. The flexibility of members 18, 20 can be selected by controlling the cross-sectional area thereof and the length of slot 16. Slot 16 allows flexible members 18, 20 to deflect inwardly under radial compressive loading. A significant increase in radial stiffness of flexible members 18, 20 occurs when they are deflected inwardly to a degree such that mating surfaces 26, 28 come in contact, at which point further deflection of flexible members 18, 20 is limited. In the preferred embodiment, the geometry of slot 16 and flexible members 18, 20 is such that the outermost diameter of opposing ribs 24 is larger than the diameter of the post 14 proximate to the platform 12 when mating surfaces 26, 28 are initially in contact.

Scaffold fixation device 10 has a centrally disposed guide wire channel 30 which extends longitudinally through fixation device 10 along the axis of post 14. Perforations 28 in the platform 12 allow fluid and cells to travel to and from the scaffold and are not limited to the shape or arrangement shown in the figures. Platform 12 may also be solid.

The cross-sectional area of flexible members 18, 20 can be controlled by selecting the width of the slot 16, as well as by the incorporation of flats 34, 36 on one or more opposing sides of flexible members 18, 20. The flats 34, 36 reduce the cross-sectional area of flexible members 18, 20 and increase their flexibility. In addition, the flats 34, 36 act as reliefs to allow the flexible members 18, 20 to flex inwardly while conforming to the confines of a hole 40 drilled in bone tissue 42 (See FIG. 4). More specifically, when a generally cylindrical object is compressed along one diameter, it expands along a diameter at 90° relative thereto. A cross-section of the compressed cylindrical object would therefore be elliptical. The flats 34, 36 truncate the ellipse (at the ends of the major axis) formed when the flexible members 18, 20 are compressed, allowing the flexible members 18, 20 to compress without the flats 34, 36 bearing against the bone tissue 42 proximate the hole 40. (See FIG. 4)

Figure 4:
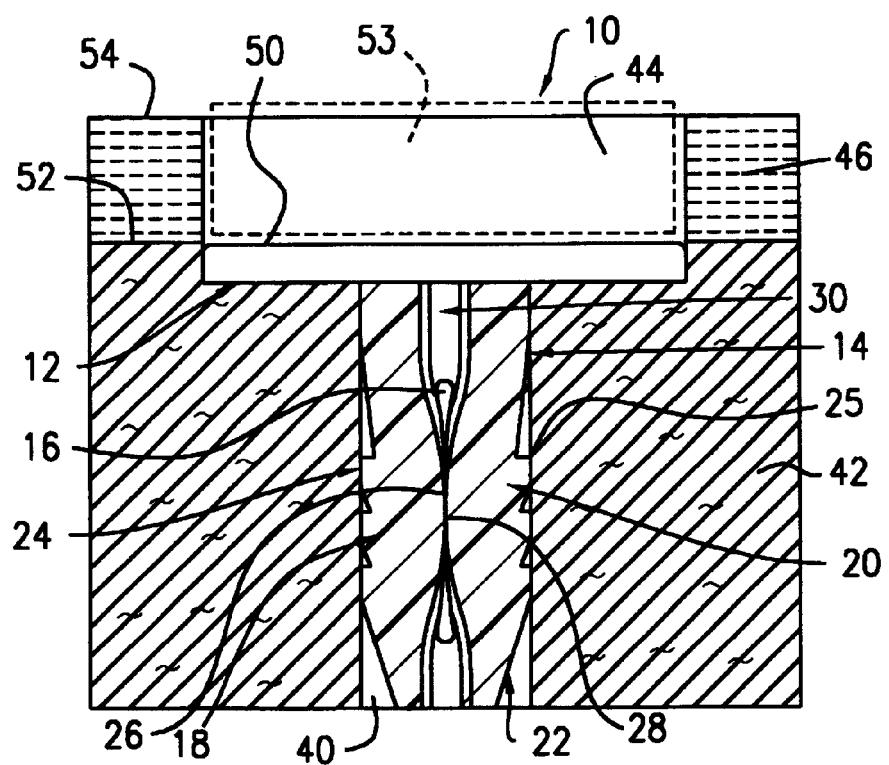
FIG. 4 is a partially cross-sectional view of the device of FIG. 1 deployed in bone.

FIG. 4 shows the surgical placement of the scaffold fixation device 10 in a hole 40 drilled in bone tissue 42. The hole 40 has a diameter establishing an interference fit between the bone tissue 42 surrounding hole 40 and the post 14, most significantly, relative to the ribs 24. Hole 40 preferably has a diameter which is less than the outermost diameter of opposing ribs 24, i.e., the tip 25-to-tip 25 distance, as would be measured by outside calipers. When the hole 40 has a diameter which is less than or equal to the diameter of post 14, mating surfaces 26, 28 of flexible members 18, 20 will come into contact during the insertion of fixation device 10 into the hole 40 causing close engagement with bone tissue 42 proximate the hole 40 through the radial deflection and radial material strain of flexible members 18, 20. When hole 40 has a diameter which is larger than the diameter of post 14 but less than the outermost diameter of ribs 24, the device 10 engages with bone tissue 42 through radial force exerted in reaction to the inward deflection of flexible members 18, 20, i.e., due to elastic memory. Flexible members 18, 20 allow the device 10 to accommodate variations in hole 40 diameter and material properties of the bone tissue 42. In very hard bone, slot 16 allows flexible members 18, 20 to deflect inwardly to conform to the hole 40 without material yield or damage occurring to post 14 or flexible members 18, 20. To install the device, 10 a hole 44 is drilled in the cartilage tissue 46 with a diameter at least as large as the outermost diameter of platform 12. The depths of hole 40 in the bone tissue 42 and the hole 44 in the cartilage 46 are selected such that, when post 14 is inserted completely into hole 40 in the bone 42, upper surface 50 of platform 12 is in alignment with or slightly below upper bone surface 52. The scaffold 53 (shown diagrammatically in dotted lines) resides within the space available within hole 44 between platform 12 and upper cartilage surface 54. Tapered tip 22 aids in introducing post 14 into hole 40. The taper 22 is reproduced in part on each rib 24 distal to the tip 25 to aid in introducing each rib 24 into the hole 40. As noted above, a surgical guide wire (not shown) may be passed through guide wire channel 30 during surgery to align scaffold fixation device 10 with the hole 40 in the bone tissue 42. After the guide wire has been used to align the tapered tip 22 with the hole 40, it is removed prior to full insertion of the post 14 to allow flexible members 18, 20 to deflect inwardly without contacting the guide wire.

Figure 5:
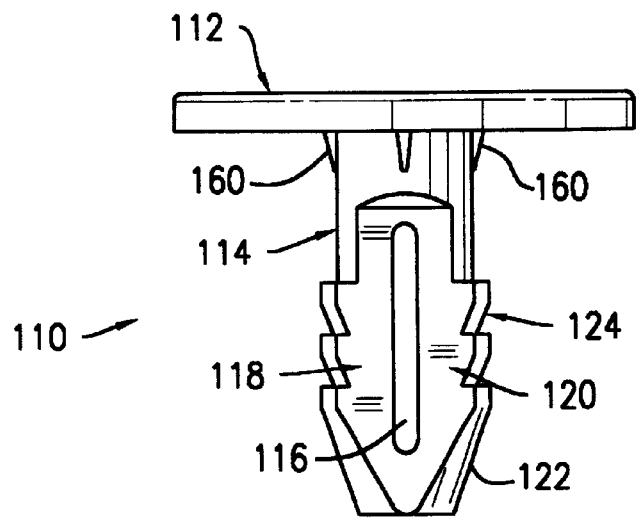
FIG. 5 is a side elevation view of a second exemplary embodiment of the present invention.
Figure 6:
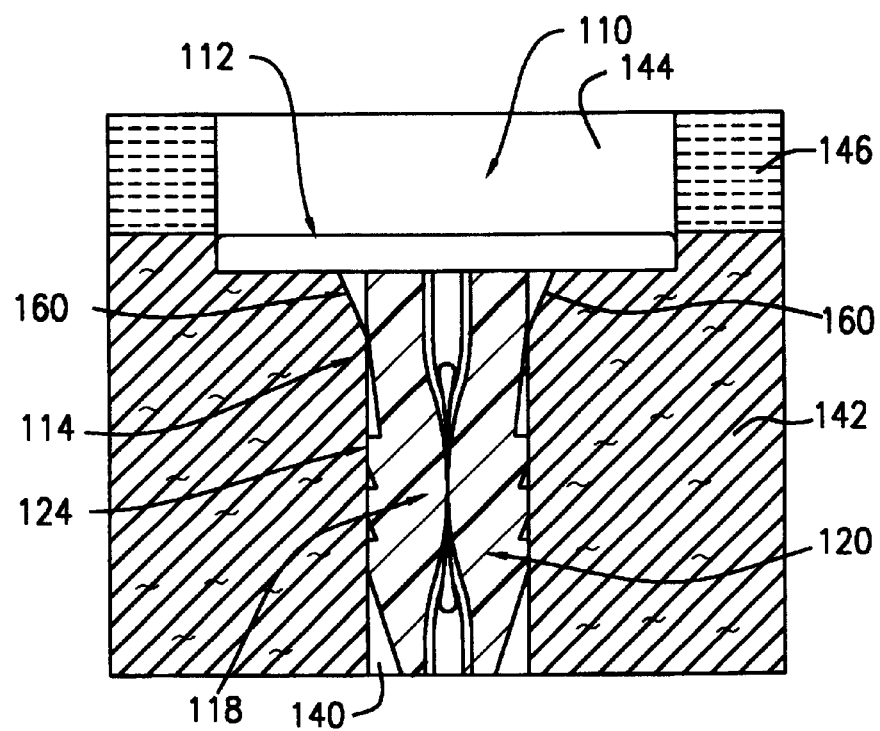
FIG. 6 is a partially cross-sectional view of the device of FIG. 5 deployed in bone.

FIG. 5 and 6 show a device 110 in accordance with an alternative embodiment of the present invention, in which post 114 has one or more vertical ribs 160 extending radially from the outer surface thereof. The vertical ribs 160 have a tapered profile similar to the taper on the tapered tip 122. When device 110 is deployed in bone tissue 142, as shown in FIG. 6, the ribs 160 cut into the bone tissue 142 surrounding hole 140 to prevent rotation of device 110 within the hole 140. Those skilled in the art will appreciate that a variety of shapes and sizes of protrusions from post 114 which make a noncircular shape will engage bone tissue 142 proximate hole 140 to prevent relative rotation of device 110 within the hole 140.

Fixation device 10, 110 may be formed from a non-porous or a partially or wholly porous material to allow cell invasion into the device 10, 110. Suitable materials from which the scaffold fixation device 10, 110 may be formed include biocompatible polymers, such as aliphatic polyesters, polyorthoesters, polyanhydrides, polycarbonates, polyurethanes, polyamides and polyalkylene oxides. The present invention also can be formed from absorbable glasses, ceramics including calcium phosphates and other biocompatible metal oxides (i.e., CaO), combinations of metals, absorbable polymers or autograft, allograft, or xenograft bone tissues.

In the preferred embodiment, the scaffold fixation device 10, 110 is formed from aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, $\epsilon$-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicyclooctane-7-one and combinations thereof. These monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

In another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors, including bone morphogenic proteins (i.e. BMP's 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-$\beta$ I–III), vascular endothelial growth factor (VEGF); and other naturally derived or genetically engineered proteins, polysaccharides, glycoproteins, or lipoproteins. These growth factors are known in the art and are described in *The Cellular and Molecular Basis of Bone Formation and Repair* by Vicki Rosen and R. Scott Thies, published by R. G. Landes Company hereby incorporated herein by reference.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

We claim:

1. A device for attaching a tissue scaffold to bone tissue, comprising:

attaching means for attaching the scaffold to said device;

retaining means coupled to said attaching means for retaining said attaching means in proximity to the bone tissue, said retaining means inserting into a hole formed in the bone tissue, said retaining means including gripping means extending from the outer periphery thereof for gripping the bone tissue proximate the hole to restrain said device from pulling away from the bone tissue, said gripping means having an interference fit relative to the hole in the bone tissue, said gripping means mounted upon a flexible member and being elastically urged into engagement with bone tissue proximate the hole, said gripping means being fully insertable into the hole in the bone tissue and having a sharp edge which engages the bone tissue proximate the hole; and anti-rotation means disposed on an outer peripheral surface of said retaining means to prevent said retaining means from rotating in the hole in the bone tissue.

2. A device for attaching a tissue scaffold to bone tissue, comprising:

a platform positionable in substantially parallel relationship to the bone tissue for retaining the tissue scaffold proximate to the bone tissue;

a post extending from the platform, said post insertable into a hole formed in the bone tissue and having a first radially displaceable flexible member and a second radially displaceable flexible member, each having a radially retracted and a radially expanded position and elastically biased to said radially expanded position, said first flexible member being spaced from said second flexible member when both are in the expanded position and abutting one another when both are in the retracted position;

a plurality of ribs disposed along a portion of the length of said post, at least one of said plurality of ribs extending from one of said first and second flexible members generally perpendicular to the axis of said post, said at least one rib positioned intermediate said platform and a distal end of said post and establishing an interference fit relative to the hole in the bone tissue with said first and second flexible members urging said at least one rib into engagement with the bone tissue to aid in preventing withdrawal of said device from a hole in the bone tissue into which it has been inserted, said post having a chamfered end to aid in the introduction of said post into the hole in the bone tissue.

3. The device of claim 2, wherein each of said plurality of ribs has a taper distal to said sharp terminal edge to aid in the introduction of said post into the hole in the bone tissue.

4. A device for attaching a tissue scaffold to bone tissue, comprising:

a platform positionable in substantially parallel relationship to the bone tissue for retaining the tissue scaffold proximate to the bone tissue;

a post extending from the platform, said post insertable into a hole formed in the bone tissue and having a first radially displaceable flexible member and a second radially displaceable flexible member, each having a radially retracted and a radially expanded position and elastically biased to said radially expanded position, said first flexible member being spaced from said second flexible member when both are in the expanded position and abutting one another when both are in the retracted position;

at least one rib extending from a surface of one of said first and second flexible members generally perpendicular to the axis of said post, said rib positioned intermediate said platform and a distal end of said post and establishing an interference fit relative to the hole in the bone tissue with said first and second flexible members urging said at least one rib into engagement with the bone tissue to aid in preventing withdrawal of said device from a hole in the bone tissue into which it has been inserted, said post having a longitudinal slot therein passing through said post and defining said first and second flexible members that are disposed on either side of said slot, said post having opposing flats in the area of said first and second flexible members, said flats limiting the contact between a peripheral surface of each of said first and second flexible members angularly offset from said at least one rib and the bone tissue proximate the hole when said device has been inserted therein.

5. The device of claim 4, wherein said at least one rib has a sharp terminal edge, said edge positionable within the hole for gripping the bone tissue to resist withdrawal of said device from the hole.

6. The device of claim 4, wherein said device has a guide wire hole extending axially there through to permit said device to be slipped over a guide wire having one end thereof positioned in the hole for guiding said device into the hole.

7. The device of claim 4, wherein said flexible members are integral with said post extending at one end from said post proximate said platform and converging at the other end in a tapered tip.

8. The device of claim 4, wherein said device is formed from a material selected from the group consisting of biocompatible polymers, absorbable polymers, glasses, ceramics, metal oxides, bone tissue and therapeutic agents, alone or in combination.

9. A device for attaching a tissue scaffold to bone tissue, comprising:

a platform positionable in substantially parallel relationship to the bone tissue for retaining the tissue scaffold proximate to the bone tissue;

a post extending from the platform, said post insertable into a hole formed in the bone tissue and having a first radially displaceable flexible member and a second radially displaceable flexible member, each having a radially retracted and a radially expanded position and elastically biased to said radially expanded position, said first flexible member being spaced from said second flexible member when both are in the expanded position and abutting one another when both are in the retracted position;

at least one rib extending from a surface of one of said first and second flexible members generally perpendicular to the axis of said post, said rib positioned intermediate said platform and a distal end of said post and establishing an interference fit relative to the hole in the bone tissue with said first and second flexible members urging said at least one rib into engagement with the bone tissue to aid in preventing withdrawal of said device from a hole in the bone tissue into which it has been inserted; and at least one vertical rib extending from a surface of said post and extending in length generally parallel to the axis of said post, said at least one vertical rib engaging the bone proximate the hole into which said device is installed to prevent rotation of the device within the hole.

10. The device of claim 9, wherein said at least one vertical rib tapers radially outwardly as it extends towards said platform.

11. The device of claim 10, wherein said at least one vertical rib includes a plurality of vertical ribs.

12. The device of claim 11, wherein said plurality of vertical ribs attach to said platform.

13. The device of claim 12, wherein said platform has a perforation therein to allow fluid and cell transmission through said perforation.

* * * * *